(12) United States Patent
Grady et al.

(10) Patent No.: US 10,181,244 B1
(45) Date of Patent: Jan. 15, 2019

(54) FLAME DETECTOR FIELD OF VIEW VERIFICATION VIA REVERSE INFRARED SIGNALING

(71) Applicant: Honeywell International Inc., Morris Plains, NJ (US)

(72) Inventors: Michael J. Grady, Mundelein, IL (US); Venus Dantas, Arlington Heights, IL (US)

(73) Assignee: Honeywell International Inc., Morris Plains, NJ (US)

( * ) Notice: Subject to any disclaimer, the term of this patent is extended or adjusted under 35 U.S.C. 154(b) by 29 days.

(21) Appl. No.: 15/648,093

(22) Filed: Jul. 12, 2017

(51) Int. Cl.
| | | |
|---|---|---|
| *G08B 17/12* | (2006.01) | |
| *G01J 5/00* | (2006.01) | |
| *G01N 21/01* | (2006.01) | |
| *G01N 21/35* | (2014.01) | |
| *G01N 21/17* | (2006.01) | |

(52) U.S. Cl.
CPC .......... *G08B 17/125* (2013.01); *G01J 5/0014* (2013.01); *G01N 21/01* (2013.01); *G01N 21/35* (2013.01); *G01N 2021/1765* (2013.01)

(58) Field of Classification Search
CPC .............................. G08B 17/005; G01J 5/0014
See application file for complete search history.

(56) References Cited

U.S. PATENT DOCUMENTS

| | | | |
|---|---|---|---|
| 6,515,285 B1 * | 2/2003 | Marshall | G01J 5/20 250/339.03 |
| 6,674,080 B2 * | 1/2004 | Trempala | G01J 5/02 250/338.1 |
| 7,714,734 B1 | 5/2010 | Billman | |
| 7,956,329 B2 | 6/2011 | Laluvein et al. | |
| 9,355,542 B2 * | 5/2016 | Bell | G01J 5/10 |
| 9,459,142 B1 | 10/2016 | Huseynov et al. | |
| 9,679,468 B2 * | 6/2017 | Piccolo, III | G08B 29/145 |

\* cited by examiner

*Primary Examiner* — Michael C Bryant
(74) *Attorney, Agent, or Firm* — Wick Phillips Gould & Martin, LLP

(57) ABSTRACT

Embodiments relate generally to systems, devices, and methods for verifying operation of an optical flame detector. A system may comprise an optical flame detector, wherein the optical flame detector comprises: a digital infrared test signal source, wherein the digital infrared test signal source is configured to transmit a digital infrared test signal; and at least one of an ultraviolet light sensor, a visible light sensor, and an infrared sensor; and an portable infrared test receiver, wherein the digital infrared test signal is receivable by the portable infrared test receiver, wherein the portable infrared test receiver is positioned to indicate whether a location of potential fire is within a field of view of the optical flame detector.

20 Claims, 3 Drawing Sheets

(12) United States Patent

FLAME DETECTOR FIELD OF VIEW VERIFICATION VIA REVERSE INFRARED SIGNALING

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

To prevent fires, the use of flame detectors may be incorporated into various environments, such as, for example, oil refineries, oil platforms/rigs, semiconductor fabrication plants, gas storage facilities, and/or power plants. These environments may require monitoring and an appropriate response to a fire or a potential fire situation. Flame detectors may detect a presence of a flame by sensing various spectral bands which may be emitted from the flame. Responses to a detected flame may include activating an alarm, shutting off a fuel line (e.g., a natural gas line), and/or triggering a fire suppression system.

SUMMARY

In an embodiment, an optical flame detector may comprise a housing, wherein the housing comprises: a digital infrared test signal source, wherein the digital infrared test signal source is configured to transmit a digital infrared test signal ("DITS"), wherein the DITS comprises at least one of a serial number of the optical flame detector, a user's mnemonic name, sensor sensitivity, time (e.g., seconds) since a last reboot of the optical flame detector, a real time clock value of the optical flame detector, and current analog optical signal levels; and at least one of an ultraviolet light sensor, a visible light sensor, and an infrared sensor.

In an embodiment, a system for verifying operation of an optical flame detector, the system may comprise: the optical flame detector, wherein the optical flame detector comprises: an infrared source, wherein the infrared source is configured to transmit a DITS; and at least one of an ultraviolet light sensor, a visible light sensor, and an infrared sensor; and a portable infrared test receiver, wherein the digital infrared test signal is receivable by the portable infrared test receiver, wherein the portable infrared test receiver is positioned to indicate whether a location of potential fire is within a field of view of the optical flame detector.

In an embodiment, a method for verifying operation of an optical flame detector, the method may comprise: positioning a portable infrared test receiver at a location of potential fire; transmitting a DITS from a digital infrared test signal source of the optical flame detector; indicating, with the portable infrared test receiver, whether the DITS is received; indicating, with the portable infrared test receiver, whether the location is within a field of view of the optical flame detector and/or that a line of sight between the location and the optical flame detector is obstructed.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
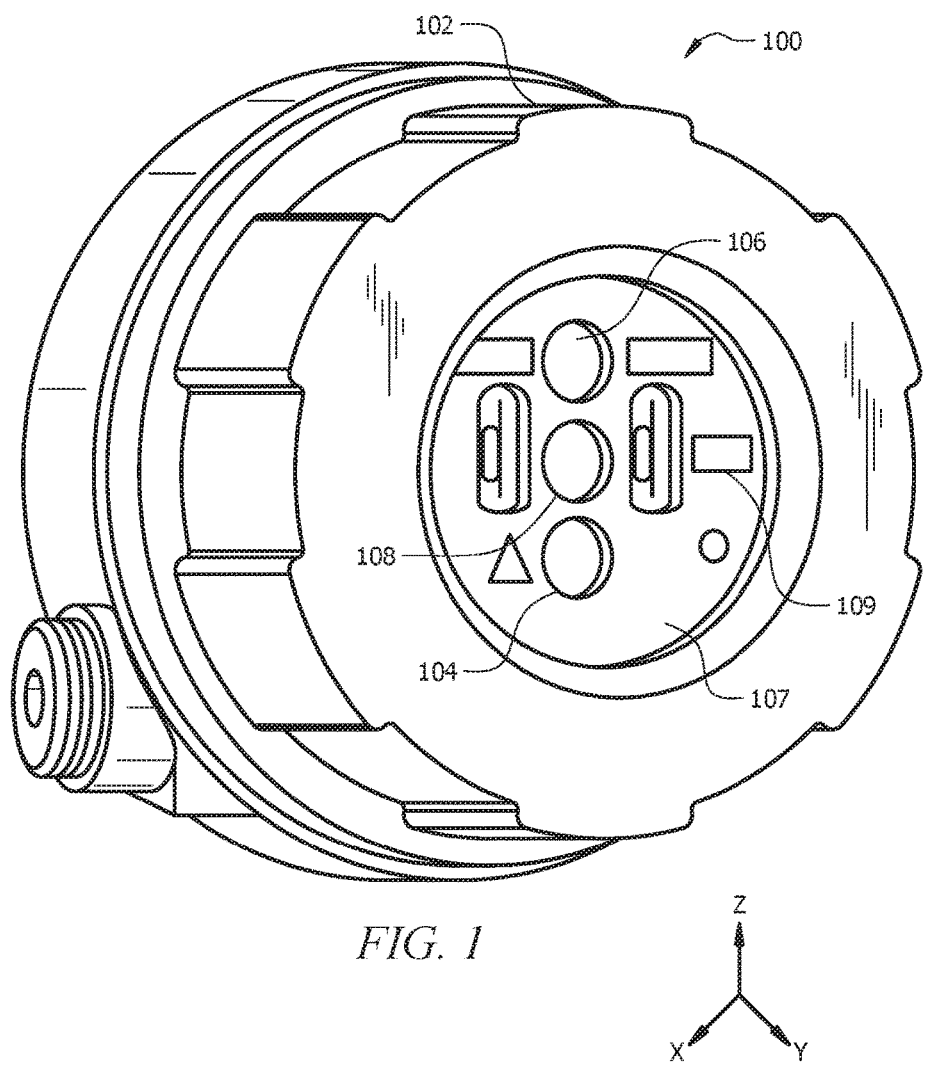
FIG. 1 is a schematic illustration of an optical flame detector in accordance with embodiments of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Optical flame detectors ("OFDs") may have an effective field of view ("FOV"), and fires within the FOV may be detected, while fires outside the FOV are not likely to be detected. During installation of an OFD, a technician may align and aim the OFD to cover an intended area.

OFDs may be checked periodically in order to confirm reliable operation. There are a number of failure modes that might prevent proper operation of the OFD. For example, failure modes that might prevent operation can include, but are not limited to: 1) a window of the OFD may become dirty or obscured; 2) the OFD may be bumped so that its aim is no longer correct; 3) additional equipment may be installed in the optical path (e.g., FOV), blocking infrared ("IR") radiation and preventing flame detection.

A conventional solution to testing the operation of an OFD may involve sending a technician out with a test lamp (e.g., test IR source). The test lamp mimics a fire. That is, the test lamp must produce light approximately as intense as light produced by a fire. The technician may activate the test lamp (e.g., aim the test lamp at the OFD) from several locations and watch for an indicator light on the OFD. This may confirm that the IR path is clear. This may require two people because a second person may be in a control room disabling a response to a flame report. Therefore, this solution may be laborious, slow, and inefficient because the test lamp may be big and heavy, and may only have a 4 meter range (i.e., the test lamp must be near the OFD). Also, the test lamp may have a modest battery life. This may be short compared to a 50-60 meter range of the OFD. As a result, the use of a test lamp may not be capable of verifying the operation of the OFD at all distances within the operating range of the OFD. Thus, this solution may not be accurate in determining whether each location is within the FOV of the OFD.

The systems, methods, and/or devices of the disclosure may utilize reverse signaling to improve a signal to noise ratio by 1) Blocking out of band radiation at a portable infrared test receiver ("PITR") with a near infrared region ("NIR") optical filter; 2) Blocking optical signals which may be modulated at an incorrect frequency relative to a digital infrared test signal ("DITS"). The DITS may utilize digital encoding (e.g., Manchester encoding). The DITS may modulate for a minority of an operation time of the OFD. That is, the DITS may be transmitted during a quiescent state of the OFD. This transmission of the DITS during the quiescent state may avoid creating a low frequency signal that might be in band for the OFD. This feature may allow the PITR to receive DITSs from multiple OFDs. Interpreting each DITS in an environment with multiple OFDs may be facilitated by both the PITR and the quiescent state DITS transmission.

The present disclosure relates to an operation verification for an OFD. Systems, methods, and/or devices of the disclosure may incorporate/embed a digital infrared test signal source in the OFD. This digital infrared test signal source may transmit a signal train (e.g., digital signal packet, DITS) to a test receiver (e.g., PITR). The DITS may include information/data such as, at least one of a serial number of the optical flame detector, a user's mnemonic name, sensor sensitivity, time (e.g., seconds) since a last reboot of the optical flame detector, a real time clock value of the optical flame detector, and current analog optical signal levels. The test receiver may be optically passive (e.g., test receiver may not transmit any signals such as a signal train). The test receiver can include a global positioning system ("GPS") and a logging capability (e.g., logging/storing data). This may make a verification procedure for OFD operation simpler. That is, a technician can simply walk to a potential flame source with the test receiver. The test receiver may then report a number of DITS it detects from various OFDs (e.g., a digital infrared test signal source of each OFD). This report can be either immediate on a display/user interface of the test receiver and/or logged/stored into an internal memory of the test receiver.

FIG. 1 is a schematic illustration of an OFD 100. The OFD 100 can include any suitable OFD configured to detect a fire/flame using optical detection techniques. In this regard, the OFD 100 serves to optically view a desired optical field for flames/fires, compose the transmitted DITS(s), and provide an alarm in the event that a flame/fire satisfying predetermined thresholds is detected. The OFD 100 may include a FOV from about 100° to about 170° relative to at least one axis (e.g., x-axis, y-axis, z-axis). The OFD 100 may detect flames at a distance ranging from about 0 meters to about 60 meters, relative to the position of the OFD 100. The OFD 100 may detect hydrocarbon and non-hydrocarbon based fires or flames. The operating temperature of the OFD 100 may be about −50° F. to about 200° F.

The OFD 100 may include a housing 102 (e.g., which can be an explosion proof housing) which may include at least one of an ultraviolet ("UV") light sensor 104, a visible light sensor 106, an infrared ("IR") sensor 108 (e.g., analog IR receiver), and a digital infrared test signal source 109. A sensitivity for each of the sensors may be adjustable.

The housing 102 may include materials, such as, for example, aluminum and/or stainless steel. The housing 102 may include a window 107 positioned to cover the UV light sensor 104, the visible light sensor 106, and/or the IR sensor 108, and digital infrared test signal source 109. The window 107 may protect the sensors and the digital infrared test signal source 109.

The digital infrared test signal source 109 (e.g., an IR source/transmitter, etc.) may emit/transmit a DITS recognizable by a test receiver. The DITS may be transmitted at an angle ranging from about 100° to about 170° relative to at least one axis (e.g., x-axis, y-axis, z-axis). That is, a spread of the DITS shall be similar to that of a coverage area included in the FOV of OFD 100. The digital infrared test signal source 109 may emit/transmit a DITS at a frequency ranging from about 30 kilohertz ("kHz") to about 60 kHz. The DITS may include data, such as, at least one of a serial number of the optical flame detector, a user's mnemonic name, sensor sensitivity, time since a last reboot of the optical flame detector, a real time clock value of the optical flame detector, and current analog optical signal levels. A transmitting range of the digital infrared test signal source 109 may substantially match that of a reception range of the OFD, and can range from about 0 meters to about 60 meters. That is, the digital infrared test signal source 109 may transmit a DITS up to a distance of about 60 meters. The DITS may be detected by a test receiver.

Figure 2:
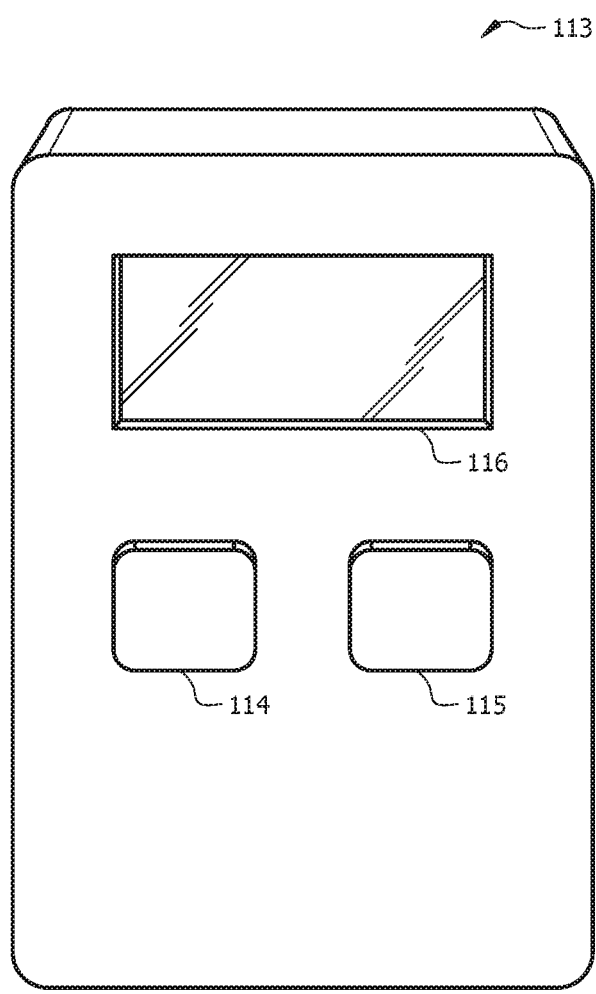
FIG. 2 is a schematic illustration of a portable infrared test receiver in accordance with embodiments of the disclosure.

FIG. 2 is a schematic illustration of PITR 113. The PITR 113 may test/verify that the OFD 100 is operating as intended (e.g., monitoring the intended coverage area). The PITR 113 may receive/process the DITS. The PITR 113 may receive electromagnetic radiation (in an NIR), wherein a wavelength of the electromagnetic radiation may be between about 700 nanometers and about 1200 nanometers. The PITR 113 may be optically passive. In certain embodiments, the PITR 113 may be a low power electronic device which may allow it to be non-incendive (e.g., incapable, under normal operating conditions, of causing ignition of a flammable gas-air, vapor-air, and/or dust-air mixture due to arcing or thermal means). The PITR 113 may include a memory 115 and a user interface 116 (e.g., liquid crystal display ("LCD")), and optionally, a positioning or location module 114 (e.g., a global positioning system (GPS) receiver and module, a time of flight (TOF) positioning system, a received signal strength (RSS) positioning system, etc.). The PITR 113 may receive and/or process DITS from distances of up to about 60 meters. For example, the PITR 113 can receive and process DITS within the transmission range of the digital infrared test signal source 109. The PITR 113 may also calculate its location/position via the location module (e.g., via the location module 114). The PITR 113 may store the data included in the DITS within memory 115 and display this data on user interface 116. That is, memory 115 may store at least one of a serial number of the OFD 100, a user's mnemonic name, sensor sensitivity, time since a last reboot of the OFD 100, a real time clock value of the OFD 100, and current analog optical signal levels. The PITR 113 can receive and store information received from each OFD 100 within range.

In some embodiments, the DITS from more than one OFD may be received by the PITR 113 at a given location. The PITR 113 may be aimed/positioned at different viewing angles at a given location in order to determine which sources (e.g., OFDs with a digital infrared test signal source) are capable of viewing the PITR 113 at the given location. For example, the PITR 113 may be within view of two or more sources. During testing, as described in more detail herein, the PITR 113 can be positioned to receive a DITS from a first source, and once the DITS information is received, repositioned/aimed to receive a DITS from a second source. This process can be repeated until each source within view is detected. This process may allow for an indication that a particular piece of equipment or location is actually within view of one or more of the OFDs. DITS may convey data for a minority of the time; contain little low-frequency components that might interfere with the flame detection; and facilitate multiple OFDs transmitting the DITS at the same time without interference without optical selection.

Figure 3:
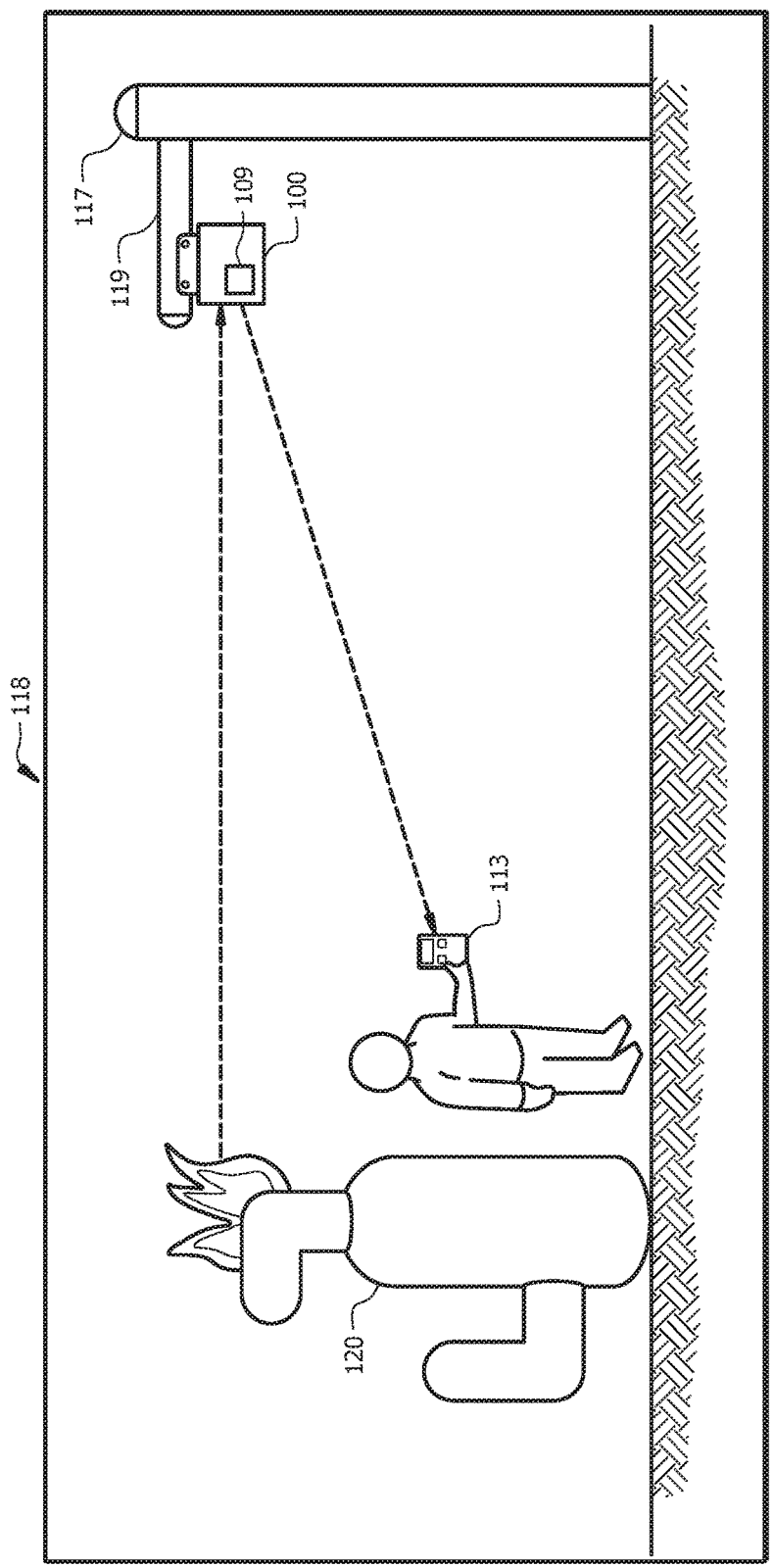
FIG. 3 is a schematic illustration of an optical flame detector operation verification system in accordance with embodiments of the disclosure.

FIG. 3 is a schematic illustration of an OFD FOV verification system 118 ("system 118"). System 118 may include the OFD 100 and the PITR 113. The OFD 100 may be positioned/installed on a structure 117 via a mount 119. The FOV of the OFD 100 may include a target area 120 (e.g., a location). That is, the OFD 100 may be installed/positioned to scan target area 120 for a flame. The OFD 100 may transmit a DITS periodically or continuously. The PITR 113 may be positioned at the target area 120. That is, to verify that target area 120 is within the FOV, a technician/user may position himself/herself with the PITR 113 at the target area 120. The target area 120 may include potential flame/fire sources, such as, for example, gas tanks, flammable materials, areas containing flammable materials, and the like.

If the FOV for the OFD 100 is correct (e.g., the potential flame source/target area is within the FOV), the PITR 113 may receive the DITS and indicate on the user interface 116 that the FOV is correct. If the FOV for the OFD 100 is incorrect (e.g., target area 120 is not within the FOV), the PITR 113 may not receive the DITS and may indicate that the FOV is incorrect on user interface 116 or not provide any indication of any received DITS. If the FOV is incorrect, a technician may correct the FOV by repositioning the OFD 100 to bring the target area 120 within the FOV. That is, based on receiving/not receiving the DITS, an indication can be made as to whether target area 120 is within the FOV of the OFD 100. For example, a green light displayed in user interface 116 may indicate if target area 120 is within the FOV of OFD 100. A red light displayed in user interface 116 may indicate if target area 120 is not within the FOV of the OFD 100.

In certain situations, window 107 (shown on FIG. 1) may become cloudy or non-transparent (e.g., obstructed) which may not allow the sensors to detect a flame and not allow the PITR 113 to receive a DITS. In this situation, the FOV may be correct, but the PITR 113 may indicate that the FOV is incorrect. A user/technician may need to examine the condition of window 107 after being notified that the FOV is incorrect, and may clean the window 107 as necessary, thereby allowing the sensors to detect a flame and allow PITR 113 to receive a DITS. In some instances, the DITS can be received, but the signal strength may be lower than expected and/or less than a threshold. Such a result may provide an indication that the FOV is correct, but that the window 107 is partially obstructed. That is, based on receiving/not receiving the DITS, an indication can be made as to whether OFD 100 is operating correctly (e.g., transmitting a DITS that is actually received). A green light displayed in user interface 116 may indicate proper/correct operation, whereas, a red light displayed in user interface 116 may indicate improper/incorrect operation.

In other scenarios, an object (e.g., equipment) may be positioned between target area 120 and OFD 100. This object may obstruct a line of sight (e.g., a signal transmission path)/FOV between the OFD 100 and the target area 120/PITR 113, and may cause the PITR 113 to indicate an incorrect FOV and may not allow OFD 100 to detect a flame. Based on receiving/not receiving the DITS, an indication can be made as to whether the line of sight between the PITR 113 and the OFD 100 is obstructed or unobstructed. A technician/user may correct positioning of the OFD 100 or reposition the object to obtain the correct FOV. A green light displayed in user interface 116 may indicate an unobstructed line of sight/FOV between the OFD 100 and target area 120/PITR 113, whereas, a red light displayed in user interface 116 may indicate an obstructed line of sight/FOV between the OFD 100 and target area 120/PITR 113.

Benefits of systems, methods, and/or devices of the disclosure may include: 1) The test receiver may contain only low-power electronics which may allow it to be made non-incendive, 2) verification/testing may only require one person, 3) flame detection may not need to be interrupted for the test/verification, 4) the verification may be focused on the flame source instead of the flame detector, 5) the range of the IR source can be comparable to the range of the OFD, and 6) the facility owner may have a reliable record (e.g., data can be stored/reviewed in the receiver) confirming staff/technicians really did perform the verification/testing.

Having described various systems and methods, various embodiments can include, but are not limited to:

In a first embodiment, an optical flame detector may comprise a housing, wherein the housing comprises: a digital infrared test signal source, wherein the digital infrared test signal source is configured to transmit a digital infrared test signal, wherein the digital infrared test signal comprises at least one of a serial number of the optical flame detector, a user's mnemonic name, sensor sensitivity, time since a last reboot of the optical flame detector, a real time clock value of the optical flame detector, and current analog optical signal levels; and at least one of an ultraviolet light sensor, a visible light sensor, and an infrared sensor.

A second embodiment may include the optical flame detector of the first embodiment, wherein the digital infrared test signal source is configured to transmit a digital infrared test signal at an angle ranging from about 100° to about 170° relative to an x-axis, a y-axis, or a z-axis.

A third embodiment may include the optical flame detector of the first or second embodiment, wherein a transmitting range for the digital infrared test signal source is about 0 meters to about 60 meters.

A fourth embodiment may include the optical flame detector of any of the preceding embodiments, wherein a transmission frequency of the digital infrared test signal is from about 30 kilohertz to about 60 kilohertz.

A fifth embodiment may include the optical flame detector of any of the preceding embodiments, wherein a field of view of the optical flame detector includes a location of potential fire.

A sixth embodiment may include the optical flame detector of any of the preceding embodiments, wherein the digital infrared test signal is receivable by a portable infrared test receiver.

A seventh embodiment may include the optical flame detector of any of the preceding embodiments, wherein the portable infrared test receiver is positioned to indicate whether the location is within the field of view of the optical flame detector.

An eighth embodiment may include the optical flame detector of any of the first through sixth embodiments and the portable infrared test receiver of the seventh embodiment, wherein the portable infrared test receiver is positioned to indicate an obstruction between the optical flame detector and the location of potential fire.

A ninth embodiment may include the optical flame detector of any of the first through sixth embodiments and the portable infrared test receiver of the seventh, or eighth embodiments, wherein the portable infrared test receiver is configured to receive electromagnetic radiation, wherein a wavelength of the electromagnetic radiation is between about 700 nanometers and about 1200 nanometers.

A tenth embodiment may include the optical flame detector of any of the first through sixth embodiments and the portable infrared test receiver of the seventh, eighth, or ninth embodiments, wherein the portable infrared test receiver is positioned to receive digital infrared test signals at a distance from about 0 meters to about 60 meters.

In an eleventh embodiment, a system for verifying operation of an optical flame detector, the system may comprise: the optical flame detector, wherein the optical flame detector comprises: a digital infrared test signal source, wherein the digital infrared test signal source is configured to transmit a digital infrared test signal; and at least one of an ultraviolet light sensor, a visible light sensor, and an infrared sensor; and a portable infrared test receiver, wherein the digital infrared test signal is receivable by the portable infrared test receiver, wherein the portable infrared test receiver is positioned to indicate whether the location of potential fire is within a field of view of the optical flame detector.

A twelfth embodiment may include the system of the eleventh embodiment, wherein the portable infrared test receiver is configured to receive electromagnetic radiation, wherein a wavelength of the electromagnetic radiation is between about 700 nanometers and about 1200 nanometers.

A thirteenth embodiment may include the system of the eleventh or twelfth embodiments, wherein a transmitting range for the digital infrared test signal source is about 0 meters to about 60 meters.

A fourteenth embodiment may include the system of any one of the eleventh through thirteenth embodiments, wherein the portable infrared test receiver is positioned to receive digital infrared test signals at a distance from about 0 meters to about 60 meters.

A fifteenth embodiment may include the system of any one of the eleventh through fourteenth embodiments, wherein the digital infrared test signal comprises at least one of a serial number of the optical flame detector, a user's mnemonic name, sensor sensitivity, time since a last reboot of the optical flame detector, a real time clock value of the optical flame detector, and current analog optical signal levels.

In a sixteenth embodiment, a method for verifying operation of an optical flame detector, the method may comprise: positioning a portable infrared test receiver at a location of potential fire; receiving a digital infrared test signal from a digital infrared test signal source of the optical flame detector; indicating, with the portable infrared test receiver, whether the digital infrared test signal is received; indicating, with the portable infrared test receiver, whether the location is within a field of view of the optical flame detector and/or that a line of sight between the location and the optical flame detector is obstructed.

A seventeenth embodiment may include the method of the sixteenth embodiment, further comprising transmitting at least one of a serial number of the optical flame detector, a user's mnemonic name, sensor sensitivity, time since a last reboot of the optical flame detector, a real time clock value of the optical flame detector, and current analog optical signal levels.

An eighteenth embodiment may include the method of the sixteenth or seventeenth embodiment, further comprising receiving, with the portable infrared test receiver, at least one of the serial number of the optical flame detector, the user's mnemonic name, the sensor sensitivity, the time since the last reboot of the optical flame detector, the real time clock value of the optical flame detector, and the current analog optical signal levels.

A nineteenth embodiment may include the method of any one of the sixteenth through eighteenth embodiments, further comprising displaying, with the portable infrared test receiver, at least one of the serial number of the optical flame detector, the user's mnemonic name, the sensor sensitivity, the time since the last reboot of the optical flame detector, the real time clock value of the optical flame detector, and the current analog optical signal levels.

A twentieth embodiment may include the method of any one of the sixteenth through nineteenth embodiments, further comprising storing, in the portable infrared test receiver, at least one of the serial number of the optical flame detector, the user's mnemonic name, the sensor sensitivity, the time since the last reboot of the optical flame detector, the real time clock value of the optical flame detector, and the current analog optical signal levels.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An optical flame detector comprising:
   a housing, wherein the housing comprises:
      a digital infrared test signal source, wherein the digital infrared test signal source is configured to transmit a digital infrared test signal, wherein the digital infrared test signal comprises at least one of: a serial number of the optical flame detector, a user's mnemonic name, sensor sensitivity, time since a last reboot of the optical flame detector, a real time clock value of the optical flame detector, and current analog optical signal levels; and
      at least one of an ultraviolet light sensor, a visible light sensor, and an infrared sensor.

2. The optical flame detector of claim 1, wherein the digital infrared test signal source is configured to transmit a digital infrared test signal at an angle ranging from about 100° to about 170° relative to an x-axis, a y-axis, or a z-axis.

3. The optical flame detector of claim 2, wherein a transmitting range for the digital infrared test signal source is about 0 meters to about 60 meters.

4. The optical flame detector of claim 3, wherein a transmission frequency of the digital infrared test signal is from about 30 kilohertz to about 60 kilohertz.

5. The optical flame detector of claim 4, wherein a field of view of the optical flame detector includes a location of potential fire.

6. The optical flame detector of claim 5, wherein the digital infrared test signal source is receivable by a portable infrared test receiver.

7. The optical flame detector of claim 6, wherein the portable infrared test receiver is positioned to indicate whether the location is within the field of view of the optical flame detector.

8. The optical flame detector of claim 7, wherein the portable infrared test receiver is positioned to indicate an obstruction between the optical flame detector and the location of potential fire.

9. The optical flame detector of claim 8, wherein the portable infrared test receiver is configured to receive electromagnetic radiation, wherein a wavelength of the electromagnetic radiation is between about 700 nanometers and about 1200 nanometers.

10. The optical flame detector of claim 9, wherein the portable infrared test receiver is positioned to receive signals at a distance from about 0 meters to about 60 meters.

11. A system for verifying operation of an optical flame detector, the system comprising:
    the optical flame detector, wherein the optical flame detector comprises:
       a digital infrared test signal source, wherein the digital infrared test signal source is configured to transmit a digital infrared test signal; and
       at least one of an ultraviolet light sensor, a visible light sensor, and an infrared sensor; and
    an portable infrared test receiver, wherein the digital infrared test signal is receivable by the portable infrared test receiver, wherein the portable infrared test receiver is positioned to indicate whether a location of potential fire is within a field of view of the optical flame detector.

12. The system of claim 11, wherein the portable infrared test receiver is configured to receive electromagnetic radiation, wherein a wavelength of the electromagnetic radiation is between about 700 nanometers and about 1200 nanometers.

13. The system of claim 12, wherein a transmitting range for the digital infrared test signal source is about 0 meters to about 60 meters.

14. The system of claim 13, wherein the portable infrared test receiver is positioned to receive signals at a distance from about 0 meters to about 60 meters.

15. The system of claim 14, wherein the digital infrared test signal comprises at least one of a serial number of the optical flame detector, a user's mnemonic name, sensor sensitivity, time since a last reboot of the optical flame detector, a real time clock value of the optical flame detector, and current analog optical signal levels.

16. A method for verifying operation of an optical flame detector, the method comprising:

positioning an portable infrared test receiver at a location of potential fire;
receiving a digital infrared test signal from a digital infrared test signal source of the optical flame detector;
indicating, with the portable infrared test receiver, whether the digital infrared test signal is received;
indicating, with the portable infrared test receiver, whether the location is within a field of view of the optical flame detector and/or that a line of sight between the location and the optical flame detector is obstructed.

17. The method of claim 16, further comprising transmitting at least one of a serial number of the optical flame detector, a user's mnemonic name, sensor sensitivity, time since a last reboot of the optical flame detector, a real time clock value of the optical flame detector, and current analog optical signal levels.

18. The method of claim 17, further comprising receiving, with the portable infrared test receiver, at least one of the serial number of the optical flame detector, the user's mnemonic name, the sensor sensitivity, the time since the last reboot of the optical flame detector, the real time clock value of the optical flame detector, and the current analog optical signal levels.

19. The method of claim 18, further comprising displaying, with the portable infrared test receiver, at least one of the serial number of the optical flame detector, the user's mnemonic name, the sensor sensitivity, the time since the last reboot of the optical flame detector, the real time clock value of the optical flame detector, and the current analog optical signal levels.

20. The method of claim 19, further comprising storing, in the portable infrared test receiver, at least one of the serial number of the optical flame detector, the user's mnemonic name, the sensor sensitivity, the time since the last reboot of the optical flame detector, the real time clock value of the optical flame detector, and the current analog optical signal levels.

* * * * *